(12) United States Patent
Muraki

(10) Patent No.: US 6,791,026 B2
(45) Date of Patent: Sep. 14, 2004

(54) BIOMEDICAL SIGNAL CABLE AND BIOMEDICAL SIGNAL PROCESSOR

(75) Inventor: Yoshiya Muraki, Hasuda (JP)

(73) Assignee: Fukuda Denshi Co., Ltd., Tokyo (JP)

(*) Notice: Subject to any disclaimer, the term of this patent is extended or adjusted under 35 U.S.C. 154(b) by 0 days.

(21) Appl. No.: 10/281,401

(22) Filed: Oct. 25, 2002

(65) Prior Publication Data

US 2004/0079542 A1 Apr. 29, 2004

(51) Int. Cl.$^7$ .............................. H01B 7/34; H04B 3/28
(52) U.S. Cl. ......................................... 174/36; 333/12
(58) Field of Search ............................... 174/36, 74 R, 174/74 A, 75 B, 76, 77 R; 333/12

(56) References Cited

U.S. PATENT DOCUMENTS

| 4,879,507 | A | * | 11/1989 | Smith | 324/207.17 |
|---|---|---|---|---|---|
| 5,334,955 | A | * | 8/1994 | Strnad | 333/12 |
| 5,549,654 | A | * | 8/1996 | Powell | 607/32 |
| 5,763,825 | A | * | 6/1998 | Gilliland | 174/36 |
| 5,796,044 | A | * | 8/1998 | Cobian et al. | 174/103 |
| 6,319,197 | B1 | * | 11/2001 | Tsuji et al. | 600/132 |

FOREIGN PATENT DOCUMENTS

| JP | 2000-151175 | * | 5/2000 | H05K/9/00 |
|---|---|---|---|---|
| JP | 2002-125943 | * | 5/2002 | A61B/5/04 |

* cited by examiner

Primary Examiner—William H. Mayo, III
(74) Attorney, Agent, or Firm—Merchant & Gould P.C.

(57) ABSTRACT

A biomedical signal cable that is applicable to also serving as an antenna for radio transmissions. The biomedical signal cable is a connects a medical telemetery having a radio transmission function and a biomedical electrode and places a selective high-resistance body with respect to a radio signal at a position away from a base of the signal cable by approximately a ¼ wavelength of the transmission frequency of the medical telemetery.

14 Claims, 6 Drawing Sheets

BIOMEDICAL SIGNAL CABLE AND BIOMEDICAL SIGNAL PROCESSOR

FIELD OF THE INVENTION

The present invention relates to a biomedical signal cable that connects a detection section that detects a biomedical signal and a biomedical signal processor capable of processing the biomedical signal detected by the detection section and transmitting the processed data by radio with a signal wire and a biomedical signal processor that uses the above described cable as an antenna wire.

BACKGROUND OF THE INVENTION

As a conventional biomedical signal processor that attaches biomedical electrodes to an examinee, collects a biomedical signal such as an electrocardiogram and transmits the collected biomedical signal by radio to a monitor device, etc., a medical telemetery apparatus is used.

This type of medical telemetery apparatus is attached to a patient when it is necessary to constantly monitor a biomedical signal like an electrocardiogram of the patient and it is more and more miniaturized out of the necessity for minimizing a burden on the patient and many portable telemetery apparatuses are currently in use.

Thus, providing a separate antenna wire for the apparatus constitutes an obstacle to the use of the apparatus. Moreover, the biomedical signal, for example, an electrocardiogram signal is a frequency not so high as a radio transmission frequency. Considering these reasons, a biomedical signal cable that connects the biomedical electrode and the medical telemetery is generally used also as an antenna for the biomedical signal processor.

However, in the case of the medical telemetery that uses the biomedical signal cable also as the antenna, the tip of the biomedical signal cable is connected to a biomedical electrode and thereby electrically connected to a living body, which causes a problem that the antenna efficiency deteriorates.

SUMMARY OF THE INVENTION

The present invention has been achieved to solve the above described problems and it is an object of the present invention to provide a biomedical signal cable which keeps high antenna efficiency when used also as an antenna wire and a biomedical signal processor using this biomedical signal cable. As means for attaining the above object, the present invention adopts, for example, the following configurations.

That is, the present invention provides a biomedical signal cable that connects a detection section that detects a biomedical signal and a biomedical signal processor capable of processing the biomedical signal detected by the detection section and transmitting the processed data by radio using a signal wire, characterized by including a first connection section connected with the biomedical signal processor and a high resistance section with high resistance for the transmission frequency, provided at a position away from the first connection section by approximately a ¼ wavelength of the transmission frequency sent by radio by the biomedical signal processor.

Alternatively, the present invention also provides a biomedical signal cable that connects a detection section that detects a biomedical signal and a biomedical signal processor capable of processing the biomedical signal detected by the detection section and transmitting the processed data by radio using a signal wire, characterized by including a first connection section connected with the biomedical signal processor and resonance sections that resonate with a transmission frequency to increase the resistance for the transmission frequency, provided at a position away from the first connection section by approximately a ¼ wavelength of the transmission frequency sent by radio by the biomedical signal processor and at a position away from the above described position by approximately a ½ wavelength of the above described transmission frequency.

Furthermore, for example, the above described resonance section is characterized to be a conductive member fixed to the signal wire. Or the conductive member of the above described resonance section is characterized to be a ferrite core. Or the conductive member of the above described resonance section is characterized to be a conductive metallic cylinder that the signal wire penetrates and electrically connected with a grounding signal wire and electrically resonating with a ¼ wavelength.

Furthermore, the above described resonance section is characterized to be formed by shaping the signal wire like an air-core coil. Or the above described resonance section is characterized in that the signal wire is shaped like an air-core coil and a parallel resonance circuit is formed by the resonance section together with an electrostatic capacitance element connected between both ends of the air-core coil of the signal wire to resonate with the resonance frequency.

Furthermore, the present invention provides a biomedical signal processor that is fed a biomedical signal from the detection section connected to the signal cable according to any one of the aforementioned embodiments via the cable, carries out predetermined processing and transmits the processing result by radio using the signal cable as an antenna.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

A biomedical signal cable according to this embodiment of the present invention, which will be described below, is a biomedical signal cable to incorporate a biomedical signal from a biomedical electrode, for example, an electrocardiogram signal into a biomedical signal processor such as a medical telemetery and is also capable of ideally serving as an antenna of the biomedical signal processor having a radio transmission function in particular.

[First Embodiment]

Figure 1:
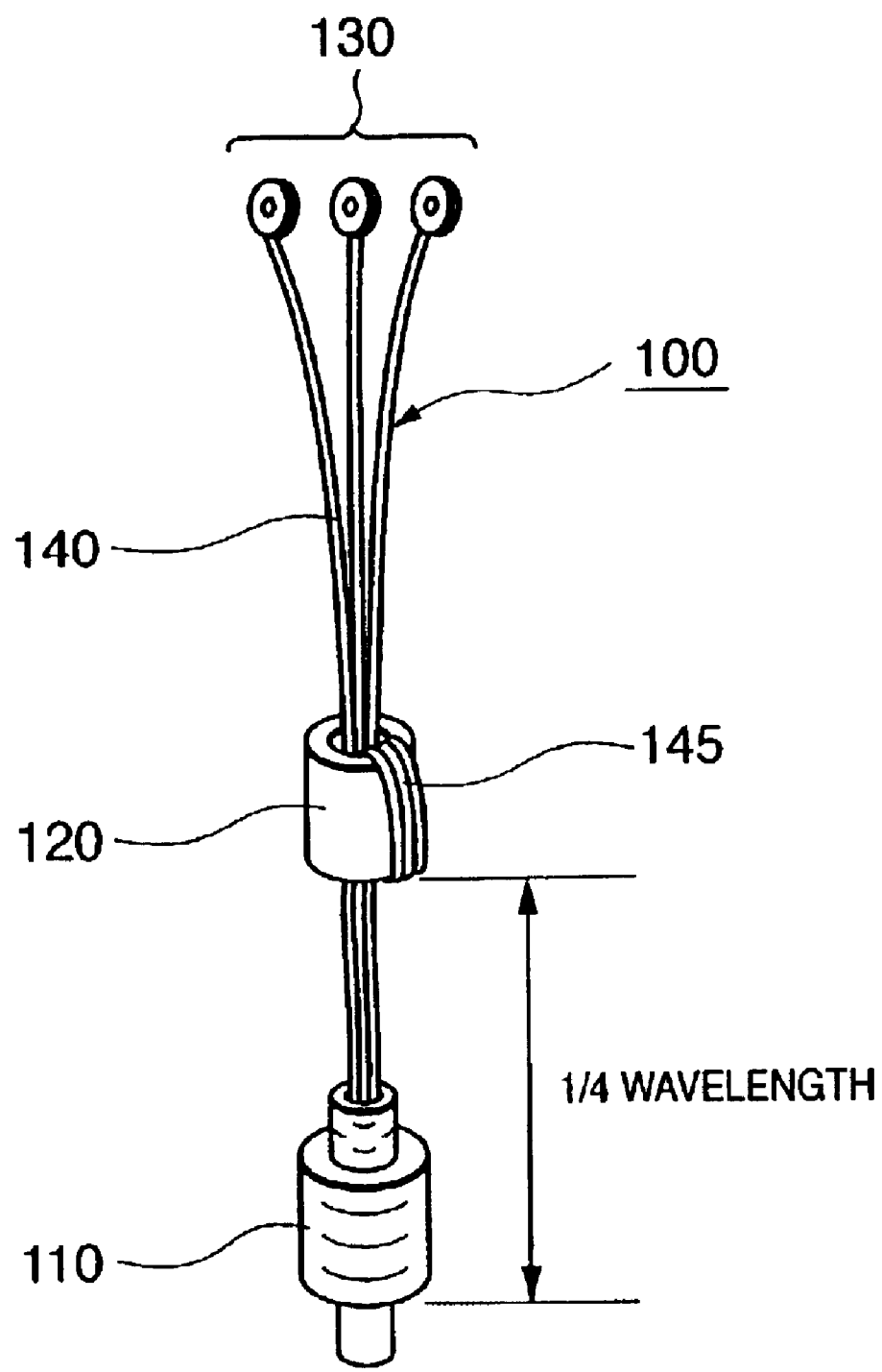
FIG. 1 is a perspective view showing a configuration example of a biomedical signal cable according to a first embodiment of the present invention.

First, FIG. 1 is a perspective view showing a configuration example of a biomedical signal cable according to a first embodiment of the present invention.

In FIG. 1, reference numeral 100 denotes a biomedical signal cable of this embodiment, 110 denotes a medical telemetery connection connector which is connected to a signal input connector provided for a medical telemetery apparatus (not shown) of the biomedical signal cable, 120 denotes a choke coil section made up of a ferrite core fixed at a position corresponding to approximately a ¼ wavelength of a transmission frequency of the medical telemetery and 130 denotes electrode connection sections to be connected to biomedical electrodes which are attached to a living body. By the way, the ends of the electrode connection sections 130 can also constitute the biomedical electrodes.

The signal cable shown in FIG. 1 is used in this embodiment because it is noted that a biomedical signal input to the medical telemetery, for example, an electrocardiogram signal is a low frequency signal and the transmission frequency of the medical telemetery apparatus is a high frequency signal.

That is, for example, even if the electrodes are connected to tips of the biomedical signal cables and electrically connected to a living body, creating a state in which the frequency band is separated and the cable is resonating with the transmission frequency is expected to improve the antenna efficiency. That is the reason why a matter with high resistance with respect to the transmission frequency (high frequency) is selectively placed in the middle of the biomedical signal cable.

It is possible to selectively use any element if it is a matter with high resistance with respect to the transmission frequency (high frequency). In the example in FIG. 1, a cylindrical ferrite core 120 is placed at a position corresponding to approximately a ¼ wavelength of the transmission frequency of the medical telemetery from the medical telemetery connection section (the end of the connector 110) and a signal wire 140 whose surface is electrically insulated is wound around this ferrite core 120 as shown by reference numeral 145. Winding the signal wire around the core section in this way reduces the possibility that core position will change and provides a biomedical signal cable with a stable characteristic.

Such a configuration described above makes it possible to create a state in which a high frequency is practically insulated at a position corresponding to approximately a ¼ wavelength of the transmission frequency λ of the medical telemetery and improve the antenna efficiency so as to produce resonance with (¼)λ.

This configuration realizes a medical telemetery system provided with high antenna performance by only replacing the biomedical signal cable that connects the medical telemetery and electrode without the need to apply special processing, etc. to the medical telemetery apparatus and biomedical electrodes.

[Second Embodiment]

The above described first embodiment has described an example where a signal wire is wound around the ferrite core fixed at a position corresponding to approximately a ¼ wavelength of a transmission frequency of the medical telemetery. However, the present invention is not limited to the above example and it is also possible to allow the signal wire to penetrate the central part of the cylindrical ferrite core and fix the signal wire at this position.

Figure 2:
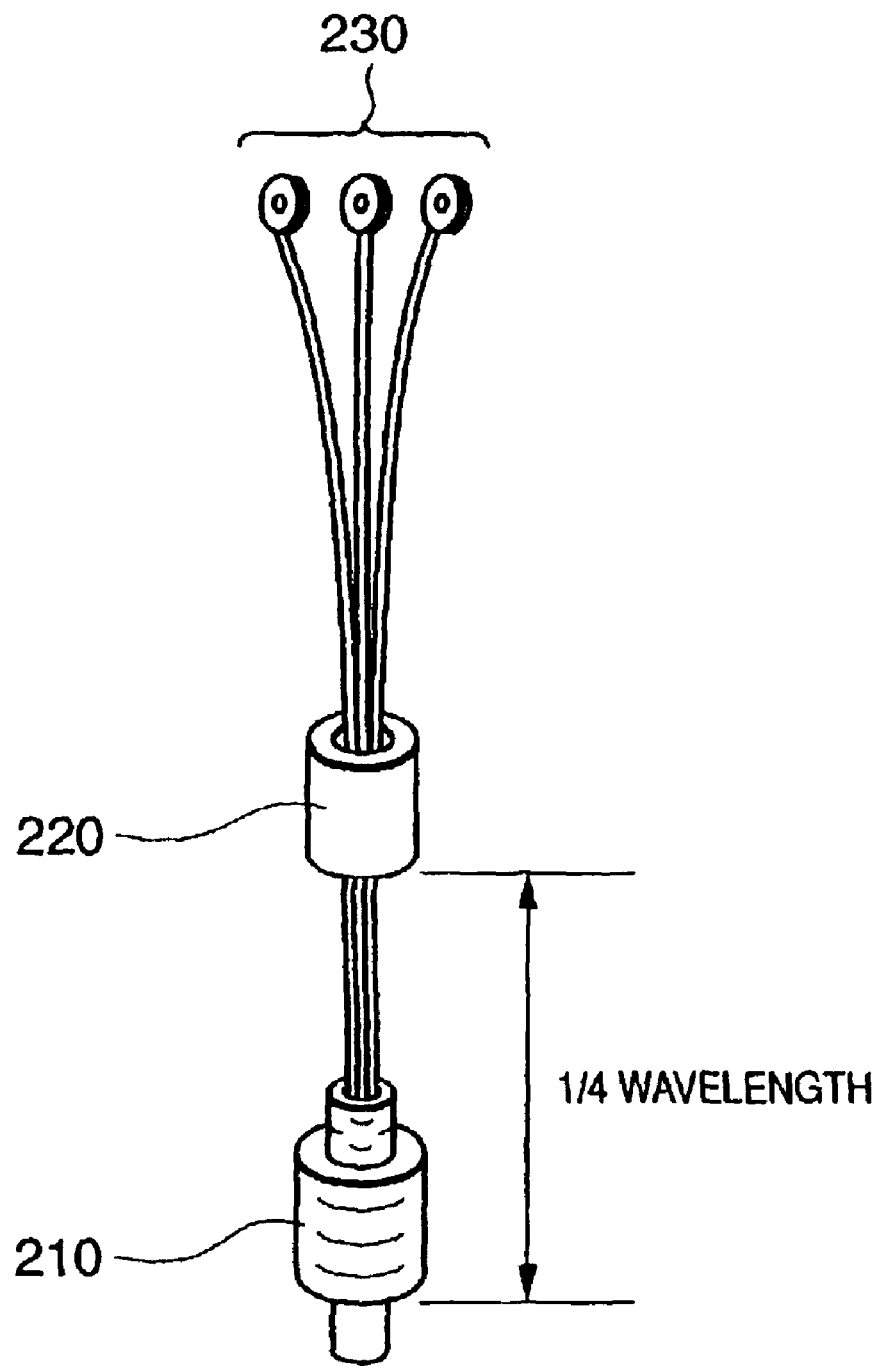
FIG. 2 is a perspective view showing a configuration example of a biomedical signal cable according to a second embodiment of the present invention.

FIG. 2 is a perspective view showing a configuration example of a biomedical signal cable according to a second embodiment of the present invention.

In FIG. 2, reference numeral 210 denotes a medical telemetery connection connector which is connected to a signal input connector provided for a medical telemetery apparatus (not shown), 220 denotes a choke coil section made up of a ferrite core fixed at a position corresponding to approximately a ¼ wavelength of a transmission frequency of the medical telemetery and 230 denotes electrode connection sections to be connected to biomedical electrodes.

The second embodiment is constructed in such a way that the ferrite core 220 is fixed to the biomedical signal cables using an adhesive to prevent displacements, for example. This configuration also provides a biomedical signal cable with high antenna performance as in the case of the first embodiment.

[Third Embodiment]

The above described first and second embodiments have described examples where a ferrite core is placed at a position corresponding to approximately a ¼ wavelength of a transmission frequency of the medical telemetery. However, the present invention is not limited to the above example and it is also possible to selectively place a high resistance component with respect to a high frequency. This embodiment is characterized in that an air-core coil is formed by the biomedical signal cable itself to achieve similar effects of operation.

Figure 3:
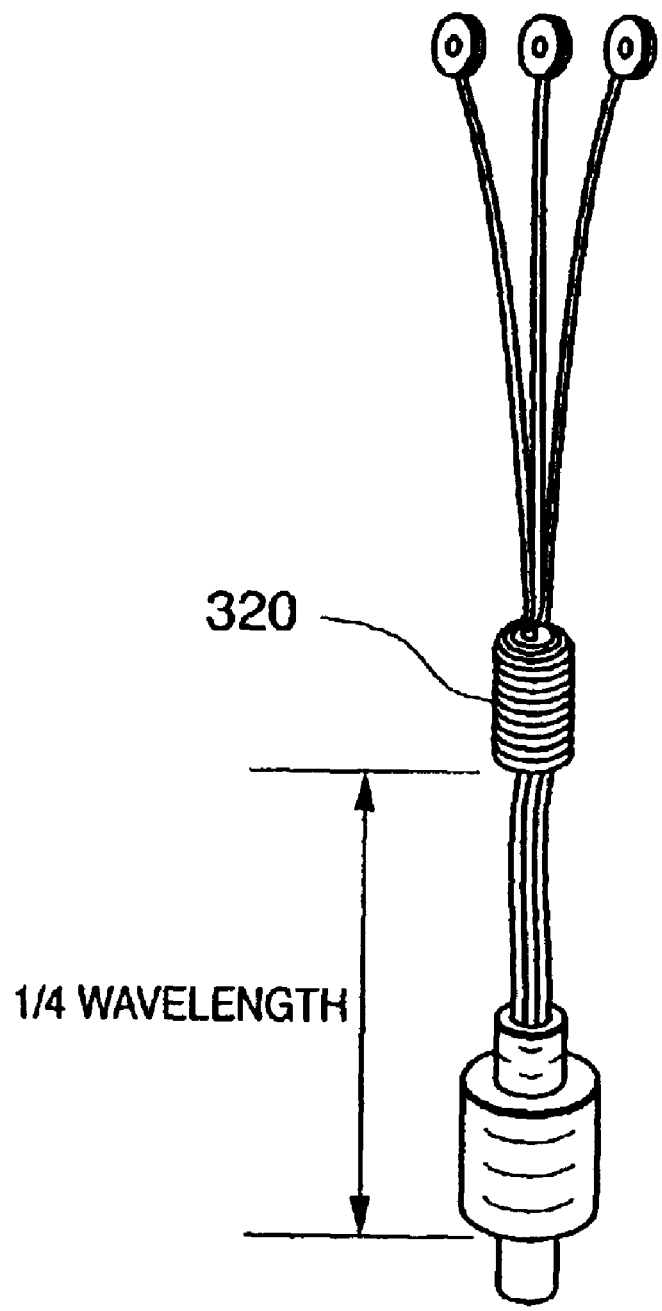
FIG. 3 is a perspective view showing a configuration example of a biomedical signal cable according to a third embodiment of the present invention.

A configuration example of the biomedical signal cable according to a third embodiment of the present invention formed in this way is shown in FIG. 3.

In FIG. 3, reference numeral 320 denotes an air-core coil composed by shaping part of the biomedical signal cable. This air-core coil 320 can be formed by, for example, shaping part of the cable like a coil and fixing the shape using an adhesive, etc. In FIG. 3, the rest of the configuration except the air-core coil 320 is similar to that of the biomedical signal cable described in the above described embodiments.

By forming the air-core coil 320 in such a way that the end of the air-core coil 320 on the telemetery side as shown in FIG. 3 is placed at a position corresponding to approximately a ¼ wavelength of the transmission frequency of the medical telemetery, it is possible to form a high resistance part with respect to a high frequency signal. As a result, similarly as the above described embodiments, a radio high frequency signal output from the medical telemetery apparatus (not shown) resonates with the air-core coil section with high resistance, making it possible to obtain a lightweight antenna with highly efficient performance without a complicated configuration.

[Fourth Embodiment]

The above described first and second embodiments have described examples where a ferrite core and air-core coil are placed at a position corresponding to approximately a ¼ wavelength of the transmission frequency of the medical telemetery. However, the present invention is not limited to the above examples and it is also possible to selectively place a high resistance component with respect to the high frequency transmission signal. This embodiment is characterized in that similar effects of operation are obtained by placing a subconductor that resonates with the transmission frequency, for example, a copper pipe or metal pipe.

Figure 4:
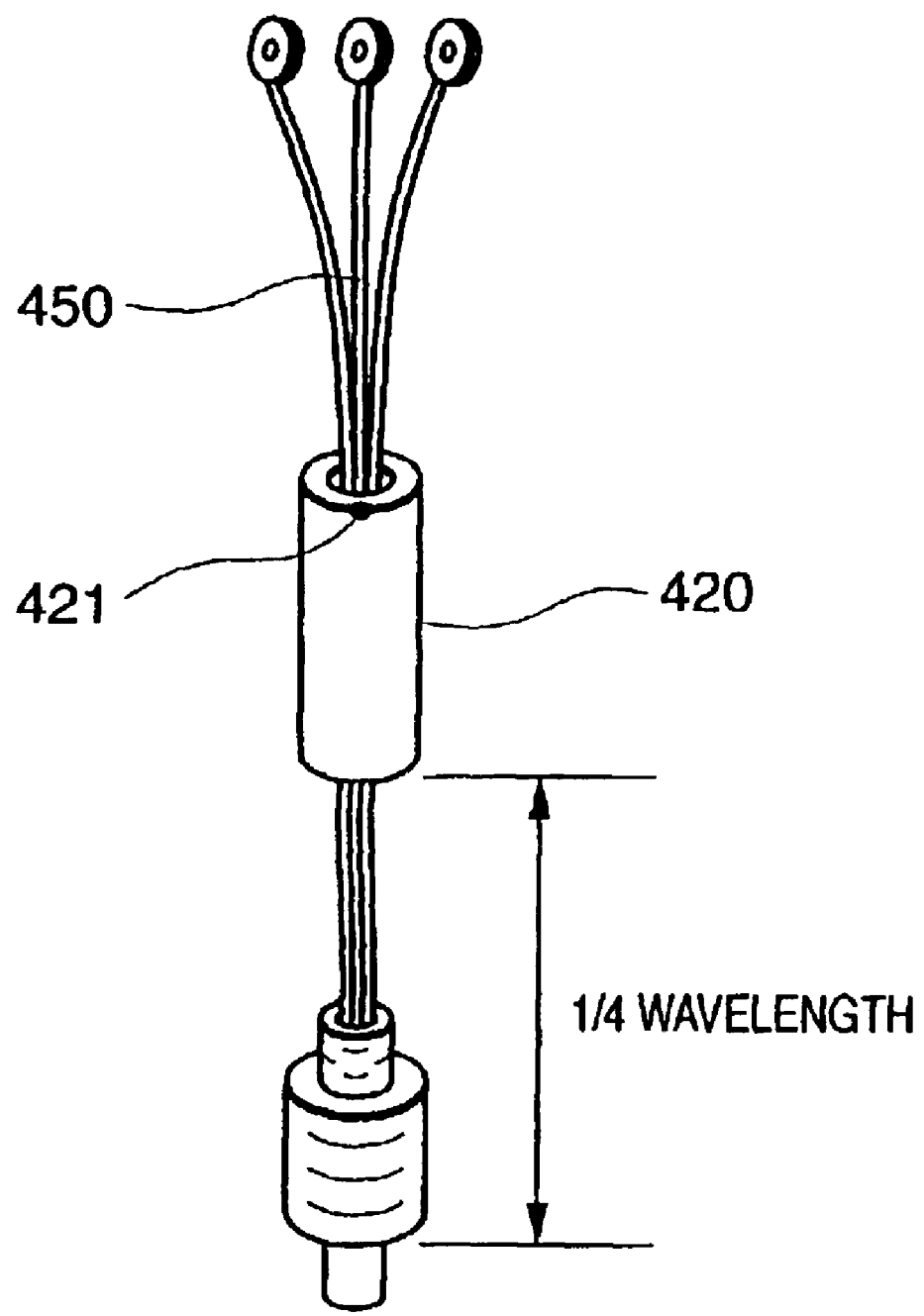
FIG. 4 is a perspective view showing a configuration example of a biomedical signal cable according to a fourth embodiment of the present invention.

A configuration example of the biomedical signal cable according to a fourth embodiment of the present invention formed in this way is shown in FIG. 4.

In FIG. 4, reference numeral 420 denotes a subconductor that electrically resonates with the transmission frequency at a ¼ wavelength and this subconductor is shaped like a ring by wrapping, for example, a copper pipe or metal foil around it. In the fourth embodiment, the biomedical signal cable is formed by a shielded wire and it is desirable to electrically connect the shielded conductor part of this shielded wire to the subconductor 420.

In the example in FIG. 4, the black bullet indicated by reference numeral 421 corresponds to the connection section between the subconductor and the shielded conductor part. The rest of the configuration is the same as that of the aforementioned embodiments.

By placing the subconductor 420 as shown in FIG. 4 at a position corresponding to approximately a ¼ wavelength of the transmission frequency of the medical telemetery, it is possible to make the subconductor 420 as the high resistance section with respect to the high frequency transmission signal, making it possible to obtain a lightweight antenna with highly efficient performance similarly as the above described embodiments.

[Fifth Embodiment]

The above described embodiments have described examples where high resistance components with respect to a high frequency signal such as a ferrite core and air-core coil are selectively placed at a position corresponding to approximately a ¼ wavelength of the transmission frequency of the medical telemetery. However, the present invention is not limited to the above examples and it is likewise possible to place high resistance components with respect to a high frequency signal at a position corresponding to approximately a ½ wavelength of the transmission frequency of the medical telemetery from the end of the high resistance component in addition to the high resistance component placed at a position corresponding to approximately a ¼ wavelength of the transmission frequency of the medical telemetery from the connection connector. By further providing a resonance subconductor in this way, it is possible to provide a signal cable having highly efficient antenna performance.

Figure 5:
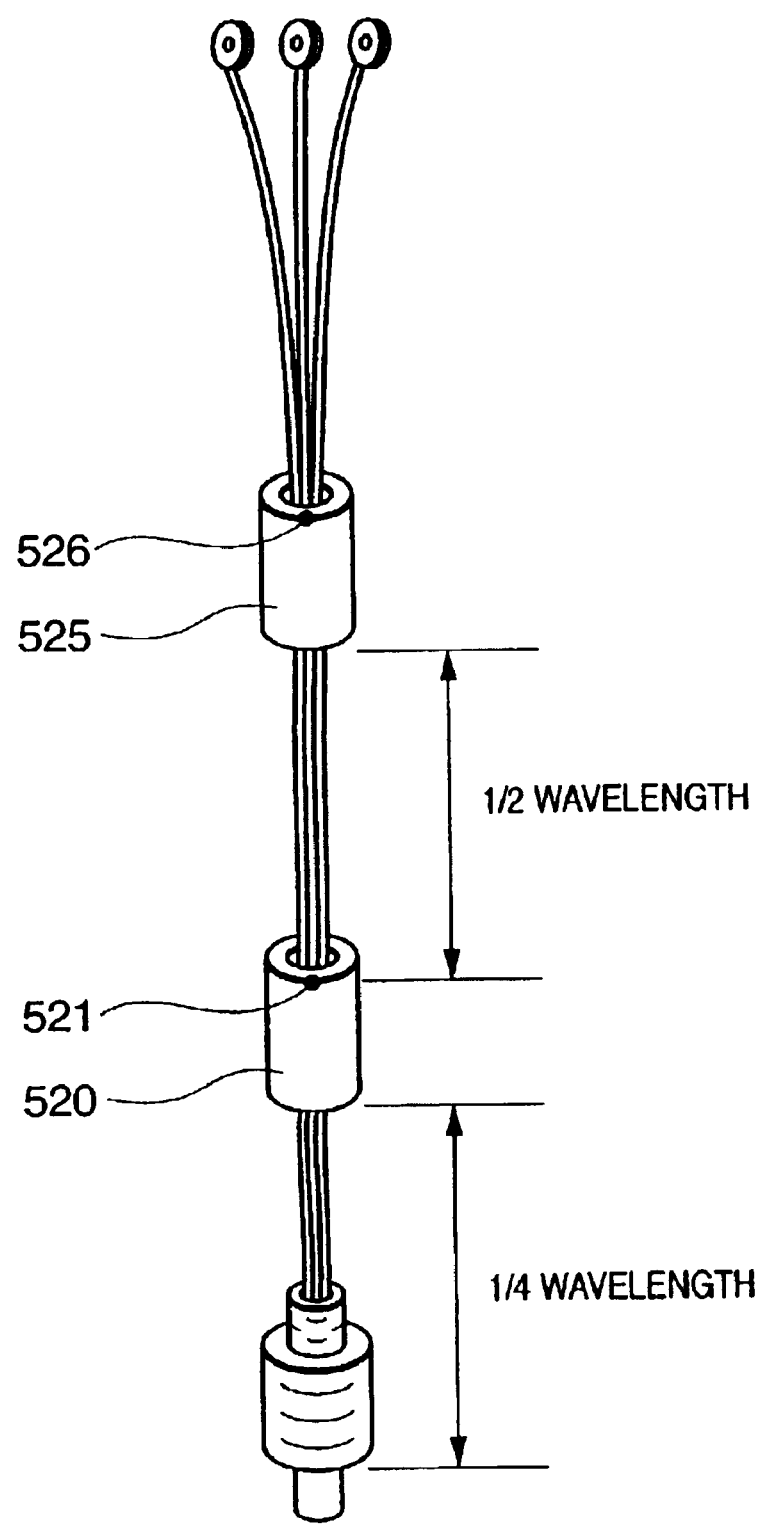
FIG. 5 is a perspective view showing a configuration example of a biomedical signal cable according to a fifth embodiment of the present invention.

A configuration example of the biomedical signal cable according to a fifth embodiment of the present invention formed in this way is shown in FIG. 5.

In FIG. 5, reference numeral 520 denotes a first subconductor that electrically resonates with the transmission frequency placed at a position corresponding to approximately a ¼ wavelength of the transmission frequency of the medical telemetery from the connection connector and this subconductor is shaped like a ring by wrapping, for example, a copper pipe or metal foil around it.

Furthermore, reference numeral 525 denotes a second subconductor that electrically resonates with the transmission frequency placed at a position corresponding to approximately a ½ wavelength of the transmission frequency of the medical telemetery from the end of the first subconductor 520 and this subconductor is shaped like a ring by wrapping, for example, a copper pipe or metal foil around it.

In the fifth embodiment as in the case of the fourth embodiment, the biomedical signal cable is formed by a shielded wire and it is desirable to electrically connect the shielded conductor part of this shielded wire with the first subconductor 520 and second subconductor 525.

In the example in FIG. 5, the black bullets indicated by reference numerals 521 and 526 correspond to the connection sections with the shielded conductor and subconductor. The rest of the configuration is the same as that of the aforementioned embodiments.

By providing the subconductors 520 and 525 as shown in FIG. 5, it is possible to form a resonance circuit at the transmission frequency and provide more efficient antenna performance.

[Sixth Embodiment]

The first embodiment has described an example where a ferrite core is fixed at a position corresponding to approximately a ¼ wavelength of the transmission frequency of the medical telemetery. However, the present invention is not limited to the above example and it is also possible to selectively place high resistance components with respect to the transmission frequency of the medical telemetery by forming a resonance circuit formed by a reactance element and inductance element at the above described position.

Figure 6:
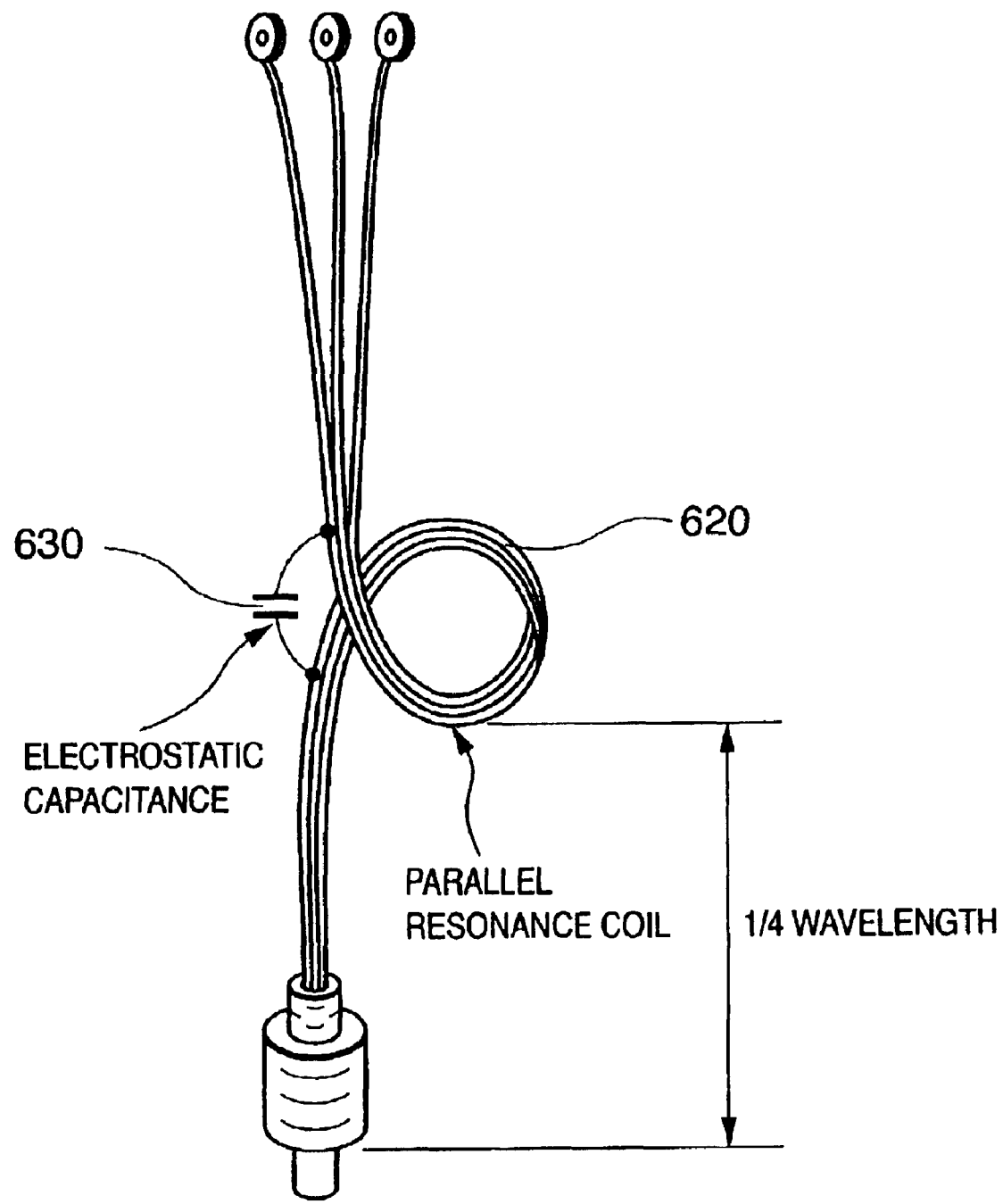
FIG. 6 is a perspective view showing a configuration example of a biomedical signal cable according to a sixth embodiment of the present invention.

A configuration example of the biomedical signal cable according to the sixth embodiment of the present invention in the such a formed configuration is shown in FIG. 6.

In FIG. 6, reference numeral 620 denotes a parallel resonance coil as an inductance element formed at a position corresponding to approximately a ¼ wavelength of the transmission frequency of the medical telemetery of the biomedical signal cable and part of the biomedical signal cable is fixed, for example, by shaping it like a circle (or may also be cylindrical as shown in FIG. 3) as illustrated. Reference numeral 630 denotes a capacitor having a predetermined electrostatic capacitance as a reactance element connected between the biomedical signal cables forming the parallel resonance coil 620.

In the sixth embodiment, this parallel resonance coil 620 and capacitor 630 form a resonance circuit corresponding to the transmission frequency of the medical telemetery.

Providing such a parallel resonance circuit allows more efficient antenna performance.

In FIG. 6, an example of connecting the capacitor 630 to secure a predetermined electrostatic capacitance has been explained, but it is also possible to selectively place high resistance components with respect to the transmission frequency of the medical telemetery at a position corresponding to approximately a ¼ wavelength of the transmission frequency of the medical telemetery, which makes it possible to secure sufficient antenna performance.

In the above explanations, the biomedical signal cable can be fixed after its formation by hardening it with synthetic resin or binding it with a binding band or using any fixing method.

[Description of Medical Telemetery]

The biomedical signal cable of each of the foregoing embodiments is applicable to a medical telemetery which performs radio communication to transfer collected information and uses the biomedical signal cable also as the transmission antenna for the radio communication, and can thereby achieve the highest effects of operation.

Each biomedical signal cable shown in FIG. 1 to FIG. 6 can be attached to the input connector section of the medical telemetery apparatus and the end of each signal cable is connected to the biomedical electrode (electrocardiogram electrode) attached to a predetermined part of the living body to collect a biomedical signal, for example, an electrocardiogram.

When a biomedical signal is collected from an examinee, the input connector of the medical telemetery is connected to the medical telemetery connection connector of the biomedical signal cable according to any one of the foregoing embodiments. Then, the biomedical electrodes are attached to predetermined parts of the examinee and the ends of the biomedical signal cables are connected to the biomedical electrodes.

Then, the medical telemetery is started and collection of a biomedical signal is started. The information of the biomedical signal is carried on a high frequency signal (modulated with the high frequency signal) and sent by ratio to a monitor device at a nurse center, etc. In this case, a radio signal is sent using the biomedical signal cable as an antenna wire.

In this case, as described above, by placing high resistance components with respect to the transmission frequency at a position corresponding to, for example, approximately a ¼ wavelength of the transmission frequency of the biomedical signal cable, it is possible to form a resonance circuit at a transmission frequency using the signal cable, allowing an efficient radio communication.

As described above, the present invention places high resistance components with respect to the transmission frequency at a position corresponding to, for example, approximately a ¼ wavelength of the transmission frequency of the biomedical signal cable, and can thereby make the transmission signal which is a high frequency signal isolated from the living body, form a resonance condition at the transmission frequency and provide an efficient radio communication with the medical telemetery that uses the biomedical signal cable also as an antenna.

Furthermore, the present invention can be applied to the system comprising either a plurality of units or a single unit. It is needless to say that the present invention can be applied to the case which can be attained by supplying programs which execute the process defined by the present system or invention.

What is claimed is:

1. A biomedical; signal cable that connects a detection section that detects a biomedical signal and a biomedical signal processor capable of processing information of a living body detected by said detection section and transmitting the processed data by radio using a signal wire, comprising:
   a first connection section connected with said biomedical signal processor; and
   a high resistance section with high resistance for the transmission frequency, provided at a position away from said first connection section by approximately a ¼ wavelength of the transmission frequency sent by radio by said biomedical signal processor.

2. The biomedical signal cable according to claim 1, wherein said resonance section is a conductive member fixed to said signal wire.

3. The biomedical signal cable according to claim 2, wherein the conductive member of said resonance section is a ferrite core.

4. The biomedical signal cable according to claim 2, wherein the conductive member of said resonance section is a conductive metallic cylinder that said signal wire penetrates and is electrically connected with a grounding signal wire and electrically resonates with a ¼ wavelength.

5. The biomedical signal cable according to claim 1, wherein said resonance section is constructed by shaping said signal wire like and air-core coil.

6. The biomedical signal cable according to claims 1, wherein said resonance section is constructed by shaping said signal wire like an air-core coil, which together with an electrostatic capacitance element connected between the end so f said air-core coil of the signal wire, forms a parallel resonance circuit that resonates with said resonance frequency.

7. A biomedical signal cable that connects a detection section that detects a biomedical signal and a biomedical signal processor capable of processing information of a living body detected by said detection section and transmitting the processed data by radio using a signal wire, comprising:
   a first connection section connected with said biomedical signal processor; and
   resonance sections that resonate with said transmission frequency, provided at a position away from said first connection section by approximately ¼ wavelength of the transmission frequency sent by radio by said biomedical signal processor and at a position away from said position by approximately a ½ wavelength of said transmission frequency.

8. The biomedical signal cable according to claim 7, wherein said resonance sections are conductive members fixed to said signal wire.

9. The biomedical signal cable according to claim 8, wherein the conductive members of said resonance sections are ferrite cores.

10. The biomedical signal cable according to claim 8, wherein the conductive members of said resonance sections are conductive metallic cylinders that said signal wire penetrates, electrically connected with a grounding signal wire and electrically resonate with a ¼ wavelength.

11. The biomedical signal cable according to claim 7, wherein said resonance sections are constructed by shaping said signal wire like and air-core coil.

12. The biomedical signal cable according to claim 7, wherein said resonance sections are constructed by shaping said signal wire like and air-core coil, which together with an electrostatic capacitance element connected between the ends of said air-core coil of the signal wire, form parallel resonance circuits that resonate with said resonance frequency.

13. A biomedical signal processor using a biomedical signal cable that connects a detection section that detects a biomedical signal and the biomedical signal processor capable of processing information of a living body detected by said detection section and transmitting the processed data by radio using a signal wire, comprising:
   processing means for incorporating a biomedical signal from said detection section connected to the biomedical signal cable via said cable and carrying out predetermined processing; and
   transmitting means for transmitting the result of said processing by radio using said signal cable as an antenna,
   wherein said biomedical signal cable comprises:
      a first connection section connected with said biomedical signal processor; and
      a high resistance section with high resistance for the transmission frequency, provided at a position away from said first connection section by approximately ¼ wavelength of the transmission frequency sent by radio by said biomedical signal processor.

14. A biomedical signal processor that uses a biomedical signal cable that connects a detection section that detects a biomedical signal and the biomedical signal processor capable of processing information of a living body detected by said detection section and transmitting the processed data by radio using a signal wire, comprising:
   processing means for incorporating a biomedical signal from said detection section connected to the biomedical signal cable via said cable and carrying out predetermined processing; and
   transmitting means for transmitting the result of said processing by radio using said signal cable as an antenna,
   wherein said biomedical signal cable comprises:
      a first connection section connected with said biomedical signal processor; and
      resonance sections that resonate with said transmission frequency, provided at a position away from said first connection section by approximately a ¼ wavelength of the transmission frequency sent by radio by said biomedical signal processor and at a position away from said position by approximately a ½ wavelength of said transmission frequency.

* * * * *